United States Patent
Guo et al.

(10) Patent No.: US 10,506,967 B2
(45) Date of Patent: Dec. 17, 2019

(54) MULTI-AXIS MEASUREMENT DEVICE FOR LOADING FORCE AND CENTER OF GRAVITY

(71) Applicant: KAOHSIUNG MEDICAL UNIVERSITY, Kaohsiung (TW)

(72) Inventors: Lan-Yuen Guo, Kaohsiung (TW); Chen-Wen Yen, Kaohsiung (TW); Lih-Jiun Liaw, Kaohsiung (TW); Jhen-Cyun Cheng, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 151 days.

(21) Appl. No.: 15/906,269

(22) Filed: Feb. 27, 2018

(65) Prior Publication Data

US 2018/0184966 A1 Jul. 5, 2018

Related U.S. Application Data

(63) Continuation of application No. PCT/CN2015/088390, filed on Aug. 28, 2015.

(51) Int. Cl.
*A61B 5/103* (2006.01)
*G01G 19/44* (2006.01)
(Continued)

(52) U.S. Cl.
CPC .......... *A61B 5/4023* (2013.01); *A61B 5/1036* (2013.01); *G01G 19/50* (2013.01);
(Continued)

(58) Field of Classification Search
CPC .......... A61B 5/4023; A61B 2562/0219; A61B 2562/0252; A61B 2562/0261;
(Continued)

(56) References Cited

U.S. PATENT DOCUMENTS

| 4,261,428 A | * | 4/1981 | Bradley | G01G 21/23 177/208 |
| 4,493,220 A | * | 1/1985 | Carignan | A61B 5/1036 73/862.628 |
| 9,255,859 B2 | * | 2/2016 | Drueding | G01L 5/161 |

FOREIGN PATENT DOCUMENTS

| CN | 101949752 A | 1/2011 |
| CN | 104083175 A | 10/2014 |

(Continued)

OTHER PUBLICATIONS

International Search Report of PCT/CN2015/088390, dated Jun. 2, 2016.

*Primary Examiner* — Randy W Gibson
(74) *Attorney, Agent, or Firm* — Locke Lord LLP; Tim Tingkang Xia, Esq.

(57) ABSTRACT

A multi-axis measurement device for loading force and center of gravity is provided comprising a first loading plate, and comprising: a first slidable element and a first piezoelectric pressure sensing element. A second loading plate comprising: a second slidable element and a second piezoelectric pressure sensing element. A connecting plate, respectively connects to the first slidable element, the first piezoelectric pressure sensing element, the second slidable element, and the second piezoelectric pressure sensing element. A plurality of third piezoelectric pressure sensing elements connects to the first loading plate. The first piezoelectric pressure sensing element measures the changes in force of the X-axis direction, the second piezoelectric pressure sensor element sensing element measures the changes in force of the Y-axis direction, and the third piezoelectric pressure sensor element sensing elements measure the changes in force of the Z-axis direction.

18 Claims, 4 Drawing Sheets

(51) Int. Cl.
  *G01G 21/23*  (2006.01)
  *G01L 1/16*  (2006.01)
  *G01L 5/00*  (2006.01)
  *A61B 5/00*  (2006.01)
  *G01G 19/50*  (2006.01)

(52) U.S. Cl.
  CPC .................. *G01L 1/16* (2013.01); *G01L 5/00* (2013.01); *A61B 2562/0219* (2013.01); *A61B 2562/0252* (2013.01); *A61B 2562/0261* (2013.01); *G01G 19/44* (2013.01); *G01G 21/23* (2013.01)

(58) Field of Classification Search
  CPC ...... A61B 5/1036; G01G 19/44; G01G 19/50; G01G 21/23; G01G 21/235; G01G 21/163; G01G 21/162; G01G 21/167; G01G 21/168; G01G 21/025; G01G 21/04; G01G 21/06; G01L 1/16; G01L 5/00
  See application file for complete search history.

(56) References Cited

FOREIGN PATENT DOCUMENTS

| | | | |
|---|---|---|---|
| JP | 2001146830 | A | 5/2001 |
| TW | 201119627 | A | 6/2011 |
| TW | M404973 | U | 6/2011 |

\* cited by examiner

MULTI-AXIS MEASUREMENT DEVICE FOR LOADING FORCE AND CENTER OF GRAVITY

CROSS-REFERENCE TO RELATED PATENT APPLICATION

This application is a continuation application of International Patent Application No. PCT/CN2015/088390, filed on Aug. 28, 2015. The disclosure of the above application is incorporated herein in its entirety by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference were individually incorporated by reference.

FIELD

The invention relates to a multi-axis measurement device for loading force and center of gravity. Specifically, the invention uses linear guideways and piezoelectric pressure sensors to substitute conventional high-priced measuring instruments that measure the ground reaction forces generated by a body standing on or moving across them.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

In modern times the rapid pace of life, high-pressure work, and irregular meal patterns adversely affect our bodies. Hence, health examinations, such as blood tests, eye examinations, and balance evaluations, become particularly important. Health examinations can also provide warnings when there are signs detected from our bodies which promotes early treatment and improved the effectiveness of health maintenance.

In the past, balance scale or functional tests, such as Berg Balance Scale and Timed Up and Go Test, were commonly used in clinics to determine a patient's balance ability. The Berg Balance Scale was developed by Katherine Berg and her colleagues early in 1989 to evaluate the functional static and dynamic balance abilities. In 1992 and 1995, the Berg Balance Scale was increasingly applied for the elderly and acute stroke patients. Research results showed excellent within-rater, between-rater reliabilities (both ICCs were 0.98) and internal consistency (Cronbach's $\alpha$=0.96). In 1996, Bogle and other researchers used this balance scale to assess balance status and fall risk among elder people. They found that those who scored less than 45 points had a higher chance of falls compared to those who scored more than 45 points. Although it didn't mean that the lower a subject scores the higher chance of falling the subject has, it still provides a cut-off point (cut-off score) to predict the possibility of falls in clinical practice. The Timed Up and Go Test was first used by Mathias and the colleagues in 1986 to study 40 elder people exhibiting balance dysfunctions. They observed the subject rising from a chair with handles, walking three meters, turning around, walking back to the chair, and sitting down. This test integrates a series of daily of activities such as from sitting to standing, walking, turning, and from standing to sitting. Although this test is a fast and useful balance function test, the scoring procedure is rough and balance function is scored on a five-point scale. Only extreme scores of 1 and 5 are scored with a more consistent consensus, while intermediate scores of 2 to 4 are less objective.

Due to the development of technology and medicine, members of society are aging in recent years. Some manual health examinations, such as eye examinations and balance evaluations, have been replaced by instruments. For instance, due to the invention of the electronic force plate, the measurement of position of center of gravity becomes more accurate. The principle of the force plate is to use uniaxial piezoelectric pressure sensors or triaxial piezoelectric pressure sensors to detect pressure signals from different directions, and convert the signals into the distribution of the position of center of gravity.

Taiwan Patent No. M404973 "THE NEW THREE-DIMENSIONAL FORCE PLATE" discloses a three-dimensional center-of-gravity position measuring force plate, including a balance board, four columns, a base plate, and four groups of pressure sensing modules that are composed of different specifications of pressure sensors, to achieve accuracy of measurement. The columns are disposed on the base plate and the groups of pressure sensors orthogonally contact the top of the columns. When an object is placed on the balance board, the force information from the X-axis, the Y-axis and the Z-axis can be collected and calculated to obtain the object's center-of-gravity position.

The three-dimensional center-of-gravity position measuring force plate as mentioned above features the modular design of pressure sensors. When an object is placed on the force plate, the force plate can capture the information of the object's center-of-gravity position. Said force plate can be applied to game machines, medical facilities, exercise measurements, and education equipment, etc.

However, the center-of-gravity measuring force plates on the market mostly use uniaxial or triaxial piezoelectric sensing elements to measure the position of center of gravity of an object. The piezoelectric sensing elements are placed in the four corners of the center-of-gravity measuring force plates, respectively, or placed at four beam columns of the center-of-gravity measuring force plates, respectively. The high-priced three-dimensional pressure sensor is currently imported. In a business point of view, it is therefore inconvenient to repair or replace the broken part once a sensor is damaged. Moreover, it is not suitable for home use and consequently the patient has to go to a hospital for examination.

Therefore, it is a common goal for businesses and developers to overcome the problems of a high-cost of electric force plate, inconvenient repair, and residential examination difficulties.

SUMMARY

The objective of the present invention aims at improving the drawbacks of available conventional center-of-gravity measuring force plates. The inventor is actively engaged in the development through continuous testing and efforts, to finally successfully develop the present invention.

In order to achieve the above and other objectives, the present invention comprises: a first loading plate, and further comprises: a first slidable element, one end of which is connected to the first loading plate and moves along a first direction; and a first piezoelectric sensing element, one end of which is connected to the first loading plate. A second loading plate further comprises a second slidable element, one end of which is connected to the second loading plate and moves along a second direction; and a second piezoelectric sensing element, one end of which is connected to the second loading plate. A connecting plate is located between the first loading plate and the second loading plate, wherein the connecting plate respectively connects to the first slidable element, the first piezoelectric sensing element, the second slidable element, and the second piezoelectric sensing element. A plurality of third piezoelectric sensing elements are connected to the first loading plate; wherein the first piezoelectric sensing element measures the changes in pressure of the first direction, the second piezoelectric sensing element measures the changes in pressure of the second direction, and the third piezoelectric sensing element measures the changes in pressure of a third direction.

An embodiment of the present invention further comprises a signal acquisition device used for capturing changes in pressure and converting it into a digital signal, and is electrically connected to the first piezoelectric sensing element, the second piezoelectric sensing element, and the third piezoelectric sensing element. A computational unit used for calculating the digital signal and generating a calculation result, is electrically connected to the signal acquisition device. A display unit used for displaying the calculation result is electrically connected to the computational unit.

An embodiment of the present invention further comprises a horizontal adjustment unit used for adjusting the horizon.

An embodiment of the present invention further comprises a weight measurement unit used for measuring weight.

An embodiment of the present invention further comprises wherein the first direction, the second direction, and the third direction are perpendicular to each other (are perpendicular mutually).

An embodiment of the present invention further comprises wherein the first slidable element is one of a linear guideway, a ball bearing guideway, a shaft type guideway, or a bearing.

An embodiment of the present invention further comprises wherein the second slidable element is one of a linear guideway, a ball bearing guideway, a shaft type guideway, or a bearing.

An embodiment of the present invention further comprises wherein the first piezoelectric sensing element is one of a strain gauge, a load cell, a piezoelectric material, an accelerometer, or any combination thereof.

An embodiment of the present invention further comprises wherein the second piezoelectric sensing element is one of a strain gauge, a load cell, a piezoelectric material, an accelerometer, or any combination thereof.

An embodiment of the present invention further comprises wherein the third piezoelectric sensing element is one of a strain gauge, a load cell, a piezoelectric material, an accelerometer, or any combination thereof.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment, and wherein.

DETAILED DESCRIPTION

In order to achieve the above objects, the following technical means and structures of the present invention are illustrated by drawings and described below. It should be noted that the described embodiments are illustrative and do not limit the present invention.

Figure 1:
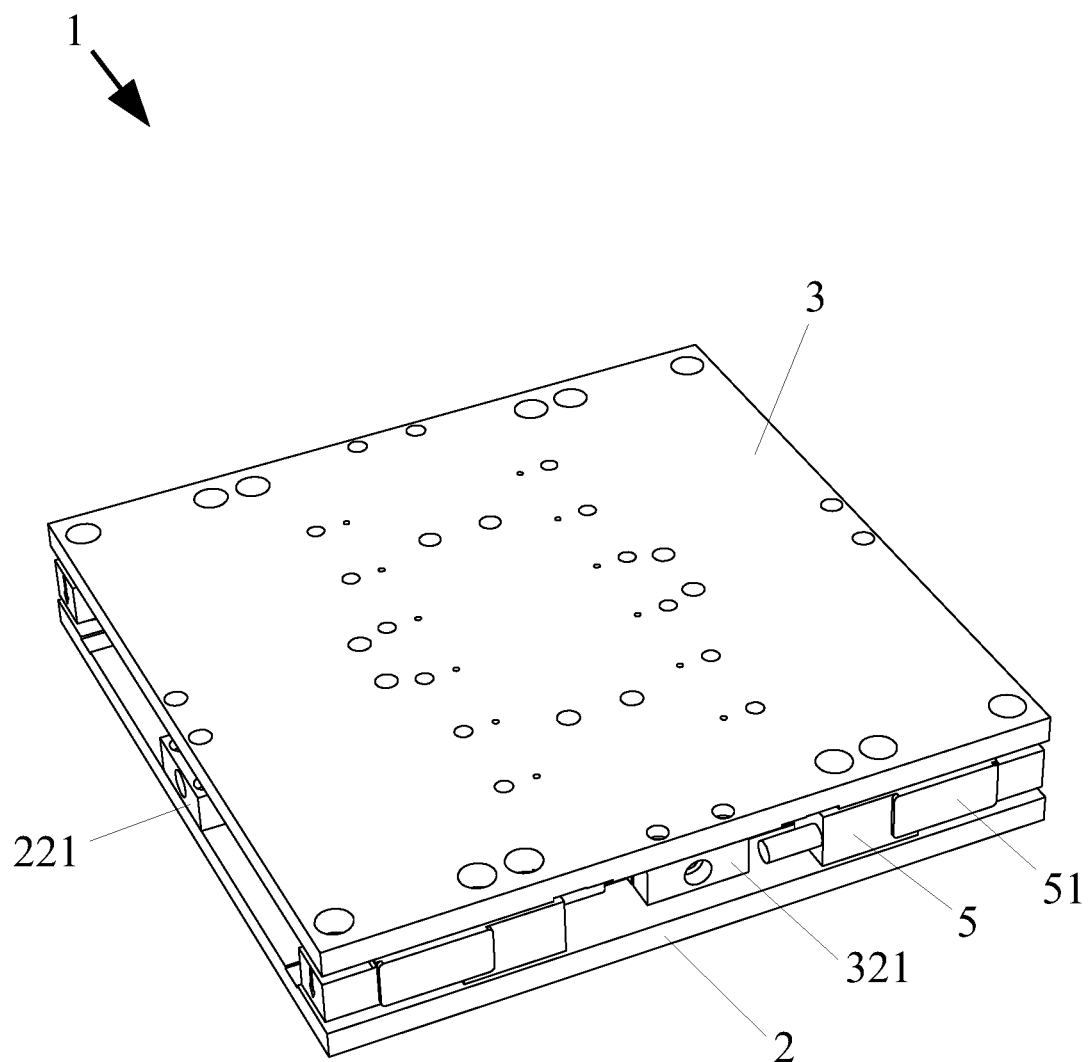
FIG. 1 is a perspective schematic view of an embodiment of the present invention.
Figure 2:
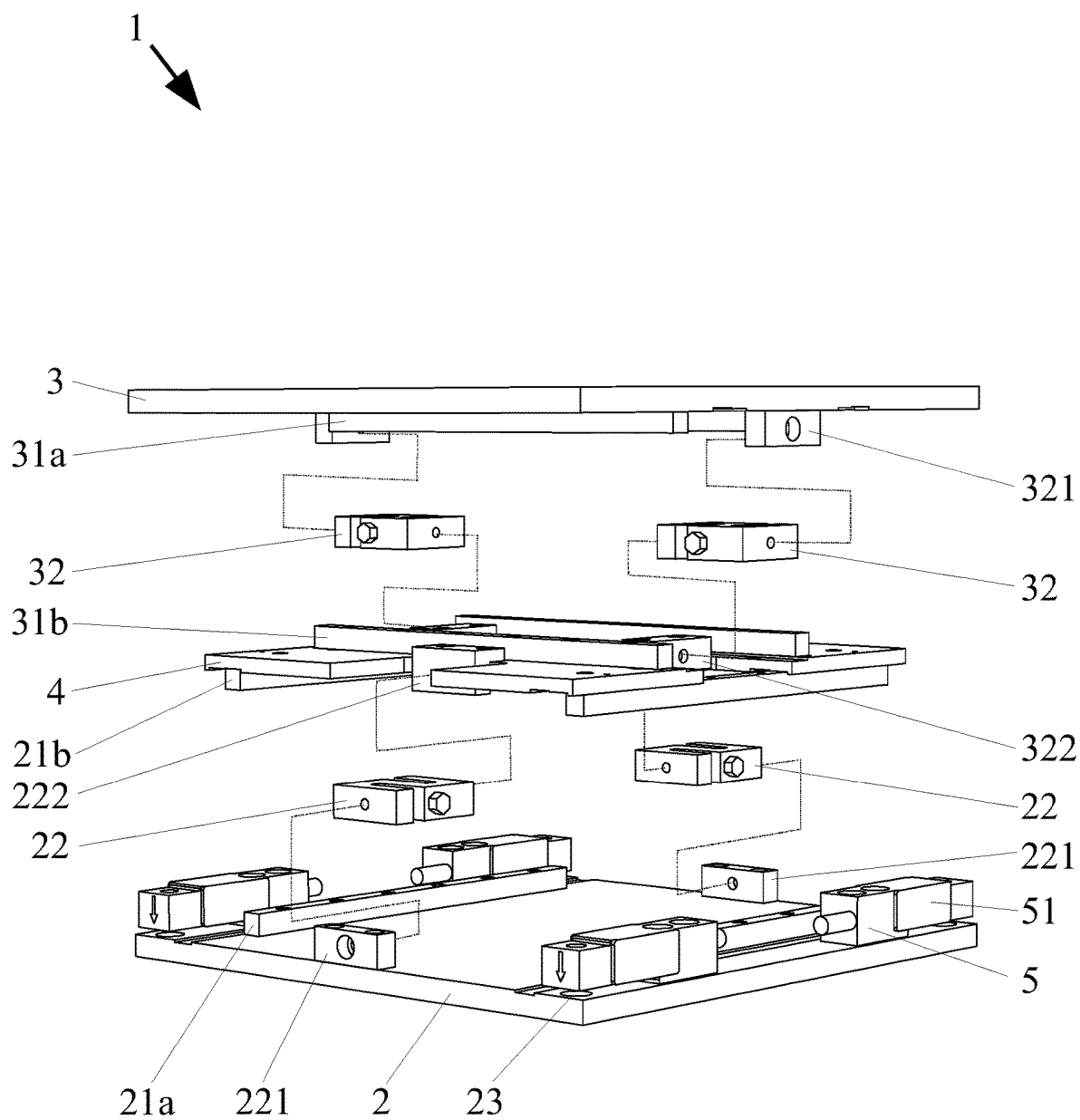
FIG. 2 is a perspective exploded view of an embodiment of the present invention.

As shown in FIG. 1 and FIG. 2, an embodiment of the present invention is illustrated in a perspective schematic view and a perspective exploded view. The multi-axis measurement device for quantifying loading force and center of gravity 1 comprises: a first loading plate 2, a second loading plate 3, a connecting plate 4, and a plurality of third piezoelectric sensing elements 5.

The first loading plate 2 can be a metal plate. The first loading plate 2 comprises: two first slidable elements (21a, 21b) and two first piezoelectric sensing elements 22.

One end of the two first slidable elements (21a, 21b) 21a is connected to the first loading plate 2, while the other end 21b is connected to a side of the connecting plate 4. When the first slidable elements (21a, 21b) encounter an external force toward a first direction (X-axis direction), the slidable elements (21a, 21b) move along the first direction. In one embodiment of the present invention, the first slidable elements (21a, 21b) are one of a linear guideway, a ball bearing guideway, a shaft type guideway, or a bearing. A user could choose guideways or bearings with different measurement accuracies depending on the user's needs.

One end of the first piezoelectric sensing elements 22 is connected to the first loading plate 2 via a connecting unit 221, while the other end is connected to the connecting plate 4 via another connecting unit 222, and the first piezoelectric sensing elements 22 are symmetrically disposed on the first loading plate 2.

When the first slidable elements (21a, 21b) encounter an external force and move along the first direction, the slidable elements (21a, 21b) simultaneously generate a force to press on the first piezoelectric sensing element 22. The first piezoelectric sensing element 22 learns the changes in pressure of the first direction while perceiving the force. Preferably, the first piezoelectric sensing element 22 is one of a strain gauge, a load cell, a piezoelectric material, an accelerometer, or any combination thereof.

The second loading plate 3 can be a metal plate. The second loading plate 3 comprises: two second slidable elements (31a, 31b) and two second piezoelectric sensing elements 32.

One end of the two second slidable elements (31a, 31b) 31a is connected to the second loading plate 3, while the other end 31b is connected to the other side of the connecting plate 4. When the second slidable elements (31a, 31b) encounter an external force toward a second direction (Y-axis direction), the slidable elements (31a, 31b) move along the second direction. In one embodiment of the present invention, the second slidable elements (31a, 31b) are one of a linear guideway, a ball bearing guideway, a shaft type guideway, or a bearing. A user could choose guideways or bearings with different measurement accuracies depending on the user's needs.

One end of the second piezoelectric sensing elements 32 is connected to the second loading plate 3 via a connecting unit 321, while the other end is connected to the connecting plate 4 via another connecting unit 322, and the second piezoelectric sensing elements 32 are symmetrically disposed on the second loading plate 3.

When the second slidable elements (31a, 31b) encounter an external force and move along the second direction, the slidable elements (21a, 21b) simultaneously generate a force to press on the second piezoelectric sensing element 32. The second piezoelectric sensing element 32 learns the changes in pressure while perceiving the force. Preferably, the second piezoelectric sensing element 32 is one of a strain gauge, a load cell, a piezoelectric material, an accelerometer, or any combination thereof.

Figure 3:
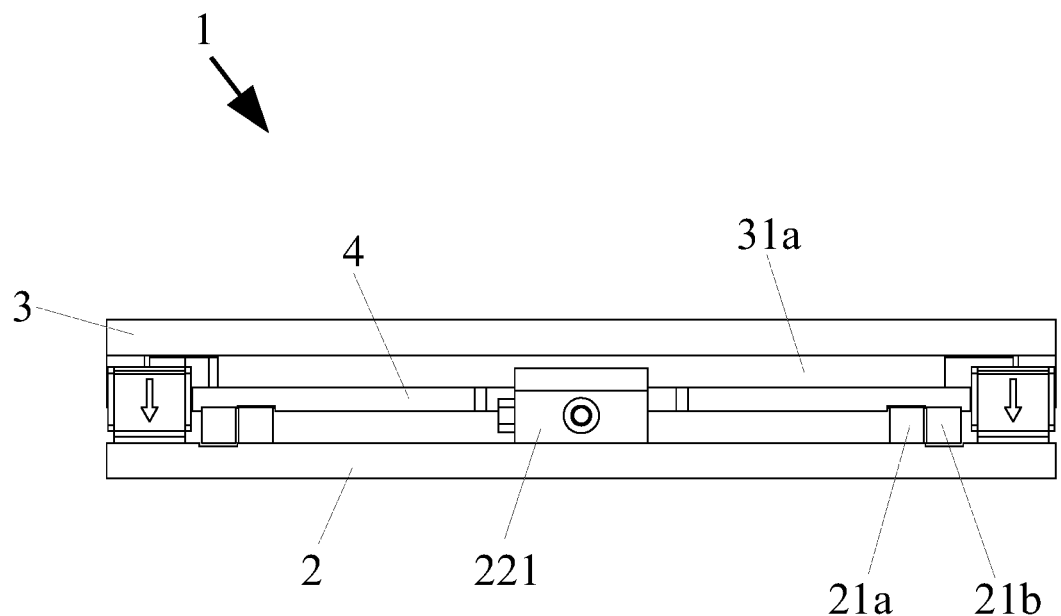
FIG. 3 is a side schematic view of an embodiment of the present invention.
Figure 4:
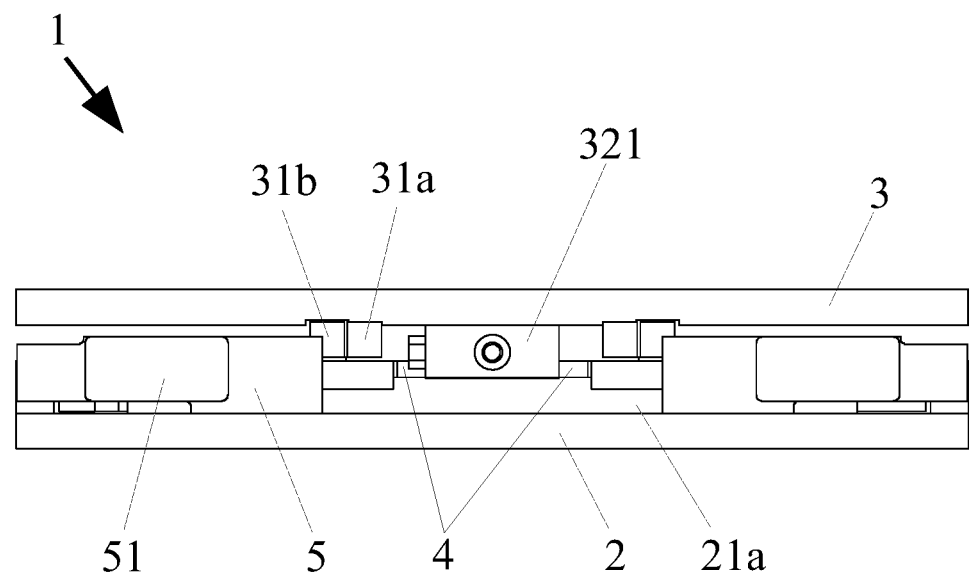
FIG. 4 is another side schematic view of an embodiment of the present invention.

As shown in FIG. 3 and FIG. 4, an embodiment of the present invention is illustrated in a side schematic view and another side schematic view. The connecting plate 4 is located between the first loading plate 2 and the second loading plate 3, wherein the connecting plate 4 can be a metal plate, and is slightly smaller than the first loading plate 2 and the second loading plate 3. The connecting plate 4 is respectively connected to the abovementioned first slidable elements (21a, 21b), the first piezoelectric sensing element 22, the second slidable elements (31a, 31b), and the second piezoelectric sensing element 32.

The third piezoelectric sensing elements 5 are connected to the first loading plate 2 to measure the changes in pressure of a third direction (Z-axis direction). In the present embodiment, the quantity of the third piezoelectric sensor elements 5 is four, and the four third piezoelectric sensing elements 5 are respectively disposed on the four corners of the first loading plate 2 in order to measure the changes in pressure of the third direction more precisely, and therefore to calculate the position of the center of gravity of the measured object. Preferably, the third piezoelectric sensing elements 5 are a strain gauge, a load cell, a piezoelectric material, an accelerometer, or any combination thereof.

Through the above-mentioned configuration, when a subject acts on the multi-axis measurement device for quantifying loading force and center of gravity 1, the first slidable elements (21a, 21b) sense the actuating force of the first direction, and conduct to the first piezoelectric sensing element 22 via the connecting plate 4. In this way, the first piezoelectric sensing element 22 can acquire the changes in pressure of the first direction. The second slidable elements (31a, 31b) sense the force of the second direction, and conduct to the second piezoelectric sensing element 32 via the connecting plate 4. In this way, the second piezoelectric sensing element 32 can acquire the changes in pressure of the second direction. The third piezoelectric sensing elements 5 sense the force of the third direction, which is generated by the subject due to gravity (i.e. weight), and the changes in pressure. Therefore, the multi-axis measurement device for quantifying loading force and center of gravity 1 can respectively measure the force signals of the first direction, the second direction, and the third direction.

In an embodiment of the present invention, the multi-axis measurement device for loading force and center of gravity 1 further comprises a weight measurement unit 51 for simultaneously measuring weight and balance performance. It is worth mentioning that the weight measurement unit 51 can be an independent mechanism or can be integrated into the third piezoelectric sensing elements 5 to carry out the measurement. Specific embodiment thereof is to sum the weights the third piezoelectric sensing elements 5 measured to obtain the subject's weight.

Figure 5:
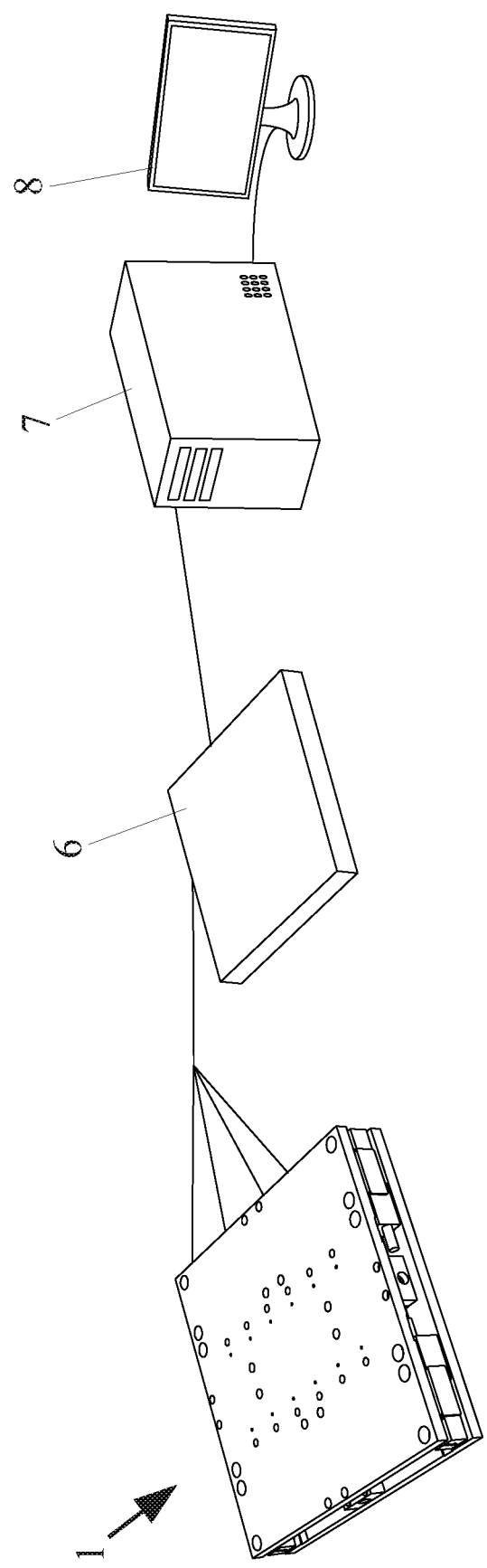
FIG. 5 is a perspective schematic view of another embodiment of the present invention.

As shown in FIG. 5, an embodiment of the present invention is illustrated in a perspective schematic view. In an embodiment of the present invention, the multi-axis measurement device for loading force and center of gravity 1 further comprises a signal acquisition device 6, a computational unit 7, and a display unit 8.

The signal acquisition device 6 is electrically connected to the first piezoelectric sensing element 22, the second piezoelectric sensing element 32, and the third piezoelectric sensing elements 5, respectively, to capture and convert changes in pressure into a digital signal.

The computational unit 7 is electrically connected to the signal acquisition device 6 to capture the digital signal and use the algorithm to assess balance capacities. The algorithm combines measurements of center of pressure (CoP) and Center of Mass (CoM) to provide an indicator of functional balance capacities.

The display unit 8 is electrically connected to the computational unit 7 to display the calculation result, real-time balance performance, and center of gravity information, etc.

In an embodiment of the present invention, the multi-axis measurement device for quantifying loading force and center of gravity 1 further comprises a horizontal adjustment unit 23, wherein the horizontal adjustment 23 is disposed on the first loading plate 2. The horizontal adjustment unit can be, but not limited to, a socket set bolt. The horizontal adjustment unit 23 can be used for adjusting the level of the whole device in order to adapt to uneven or tilting ground or surfaces.

To conclude, comparing the present invention which quantifies loading force and center of gravity, to the conventional technique, the present invention has the following advantages: The present invention of the multi-axis measurement device for quantifying loading force and center of gravity uses linear guideway and piezoelectric sensing elements as substitutes for high-priced electric three-dimensional sensors, so that the manufacturing cost is reduced, and home-based usage is more practical. The component parts of the multi-axis measurement device for quantifying loading force and center of gravity of the present invention are sold retail; hence the repair and maintenance are convenient and cost effective. The present invention of the multi-axis measurement device for quantifying loading force and center of gravity can use slidable elements with different measurement accuracies depending on the user's needs, hence has better adaptability and are easier to use, compared to the commercial triaxial force plate.

Although the present invention is disclosed above by feasible preferred embodiments, the preferred embodiments are not restrictive of the claims of the present invention. Equivalent implementation and changes made by persons skilled in the art to the preferred embodiments without departing from the spirit of the present invention must be deemed falling within the scope of the present invention.

What is claimed is:

1. A multi-axis measurement device for loading force and center of gravity comprising:
   a first loading plate, further comprising:
      a first slidable element, wherein one end of the first slidable element is connected to the first loading plate, and moves in a first direction; and
      a first piezoelectric pressure sensing element, wherein one end of the first piezoelectric pressure sensing element is connected to the first loading plate;
   a second loading plate, further comprising:
      a second slidable element, wherein one end of the second slidable element is connected to the second loading plate, and moves in a second direction; and
      a second piezoelectric pressure sensing element, wherein one end of the second piezoelectric pressure sensing element is connected to the second loading plate;
   a connecting plate, located between the first loading plate and the second loading plate, wherein the connecting plate is respectively connected to the first slidable element, the first piezoelectric pressure sensing element, the second slidable element, and the second piezoelectric pressure sensing element; and
   a plurality of third piezoelectric pressure sensing elements, connected to the first loading plate;
   wherein the first piezoelectric pressure sensing r element measures the changes in pressure of the first direction, the second piezoelectric pressure sensing element measures the changes in pressure of the second direction, and the third piezoelectric pressure sensing elements measure the changes in pressure of a third direction.

2. The multi-axis measurement device for loading force and center of gravity according to claim 1, further comprising:
   a signal acquisition device, electrically connected to the first piezoelectric pressure sensing element, the second piezoelectric sensor element, and the third piezoelectric pressure sensing elements, to capture changes in pressure and convert the changes in pressure into a digital signal;
   a computational unit, electrically connected to the signal acquisition device to calculate the digital signal and generate a calculation result; and
   a display unit, electrically connected to the computational unit to display the calculation result.

3. The multi-axis measurement device for loading force and center of gravity according to claim 2, further comprising a horizontal adjustment unit to adjust the horizon placement.

4. The multi-axis measurement device for loading force and center of gravity according to claim 2, further comprising a weight measurement unit to measure weight.

5. The multi-axis measurement device for loading force and center of gravity according to claim 2, wherein the first direction, the second direction, and the third direction are perpendicular mutually.

6. The multi-axis measurement device for loading force and center of gravity according to claim 2, wherein the first slidable element is one of a linear guideway, a ball bearing guideway, a shaft type guideway, or a bearing.

7. The multi-axis measurement device for loading force and center of gravity according to claim 2, wherein the second slidable element is one of a linear guideway, a ball bearing guideway, a shaft type guideway, or a bearing.

8. The multi-axis measurement device for loading force and center of gravity according to claim 2, wherein the first piezoelectric sensor element is one of a strain gauge, a load cell, a piezoelectric material, an accelerometer, or any combination thereof.

9. The multi-axis measurement device for loading force and center of gravity according to claim 2, wherein the second piezoelectric sensor element is one of a strain gauge, a load cell, a piezoelectric material, an accelerometer, or any combination thereof.

10. The multi-axis measurement device for loading force and center of gravity according to claim 2, wherein the third piezoelectric sensor element is one of a strain gauge, a load cell, a piezoelectric material, an accelerometer, or any combination thereof.

11. The multi-axis measurement device for loading force and center of gravity according to claim 1, further comprising a horizontal adjustment unit to adjust the horizon placement.

12. The multi-axis measurement device for loading force and center of gravity according to claim 1, further comprising a weight measurement unit to measure weight.

13. The multi-axis measurement device for loading force and center of gravity according to claim 1, wherein the first direction, the second direction, and the third direction are perpendicular mutually.

14. The multi-axis measurement device for loading force and center of gravity according to claim 1, wherein the first slidable element is one of a linear guideway, a ball bearing guideway, a shaft type guideway, or a bearing.

15. The multi-axis measurement device for loading force and center of gravity according to claim 1, wherein the second slidable element is one of a linear guideway, a ball bearing guideway, a shaft type guideway, or a bearing.

16. The multi-axis measurement device for loading force and center of gravity according to claim 1, wherein the first piezoelectric sensor element is one of a strain gauge, a load cell, a piezoelectric material, an accelerometer, or any combination thereof.

17. The multi-axis measurement device for loading force and center of gravity according to claim 1, wherein the second piezoelectric sensor element is one of a strain gauge, a load cell, a piezoelectric material, an accelerometer, or any combination thereof.

18. The multi-axis measurement device for loading force and center of gravity according to claim 1, wherein the third piezoelectric sensor element is one of a strain gauge, a load cell, a piezoelectric material, an accelerometer, or any combination thereof.

* * * * *